US00PP25307P2

(12) United States Plant Patent
Iredell et al.

(10) Patent No.: US PP25,307 P2
(45) Date of Patent: Feb. 24, 2015

(54) ***BOUGAINVILLEA* PLANT NAMED 'IREBABS2'**

(50) Latin Name: *Bougainvillea×spectro-glabra*
Varietal Denomination: IREBABS2

(71) Applicants: Janet Willa Iredell, Brisbane (AU); Peter Dawborn Iredell, Brisbane (AU)

(72) Inventors: Janet Willa Iredell, Brisbane (AU); Peter Dawborn Iredell, Brisbane (AU)

( * ) Notice: Subject to any disclaimer, the term of this patent is extended or adjusted under 35 U.S.C. 154(b) by 0 days.

(21) Appl. No.: 13/998,993

(22) Filed: Dec. 31, 2013

(51) Int. Cl.
*A01H 5/00* (2006.01)

(52) U.S. Cl.
USPC ..... Plt./256

(58) Field of Classification Search
USPC ..... Plt./256
See application file for complete search history.

*Primary Examiner* — Anne Grunberg
(74) *Attorney, Agent, or Firm* — Barbara Campbell; Cochran Freund & Young LLC

(57) ABSTRACT

A *Bougainvillea* plant particularly distinguished by a rounded, low growing, prostrate, and spreading shrub and having rose-colored bracts, is disclosed.

3 Drawing Sheets

Genus and species: *Bougainvillea×spectro-glabra.*
Variety denomination: 'IREBABS2'.

BACKGROUND OF THE NEW PLANT

The present invention comprises a new and distinct variety of *Bougainvillea*, botanically known as *Bougainvillea×spectro-glabra*, and hereinafter referred to by the variety name 'IREBABS2'. The new variety originated from an open-pollination between the female *Bougainvillea* 'Kayata' (unpatented) and unknown male *Bougainvillea* in October 1996. A single plant selection was subsequently chosen in May 1998 for further evaluation and asexual propagation.

The new plant was first asexually propagated October 1998 in Brisbane, Australia and has been asexually reproduced by cuttings for numerous generations in Brisbane, Australia. The present invention has been found to retain its distinctive characteristics through successive asexual propagations by cuttings.

'IREBABS2' has not been made publicly available or sold more than one year prior to the filing of this application.

SUMMARY OF THE INVENTION

The following are the most outstanding and distinguishing characteristics of the new variety when grown under normal horticultural practices in Brisbane, Australia.

1. A rounded, low growing, prostrate, and spreading shrub; and
2. Having rose-colored bracts.

DESCRIPTION OF THE PHOTOGRAPHS

This new *Bougainvillea* plant is illustrated by the accompanying photographs which show the overall habit, foliage, reproductive organs and colored bracts of the plant. The colors are as true as can be reasonably obtained by conventional photographic procedures. The photographs are of an approximately ten-year-old plant grown outdoors in Brisbane, Australia.

DESCRIPTION OF THE NEW VARIETY

Figure 1:
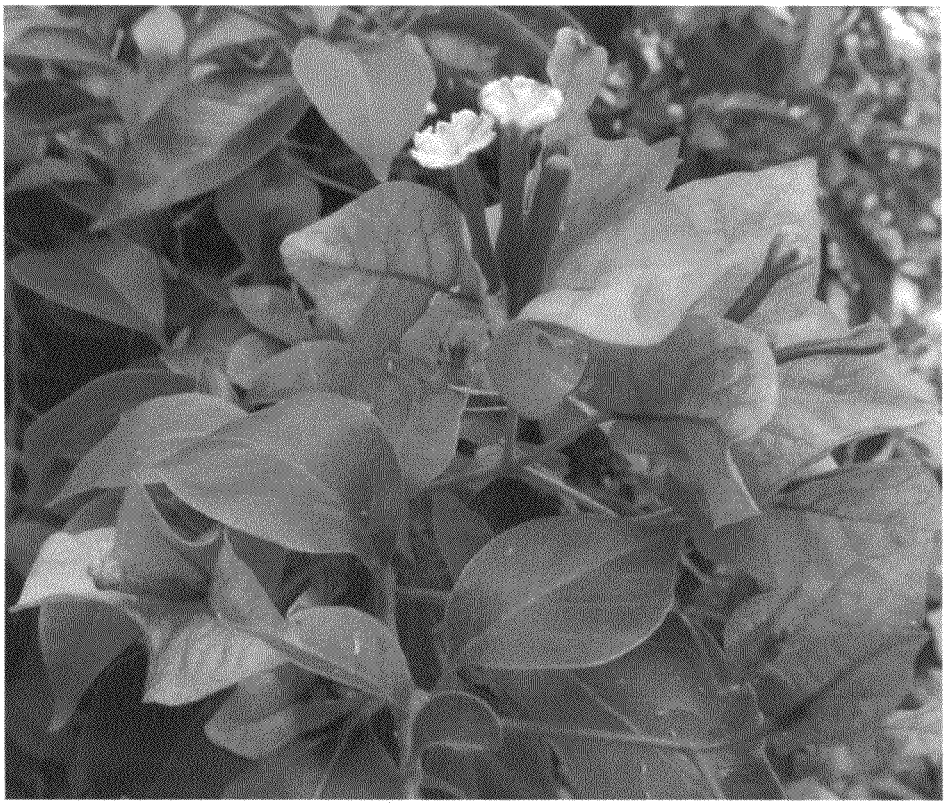
FIG. 1 shows a close-up the foliage, flower buds, colored bracts, and grey-yellow and grey-purple flowers taken in May 2014.
Figure 2:
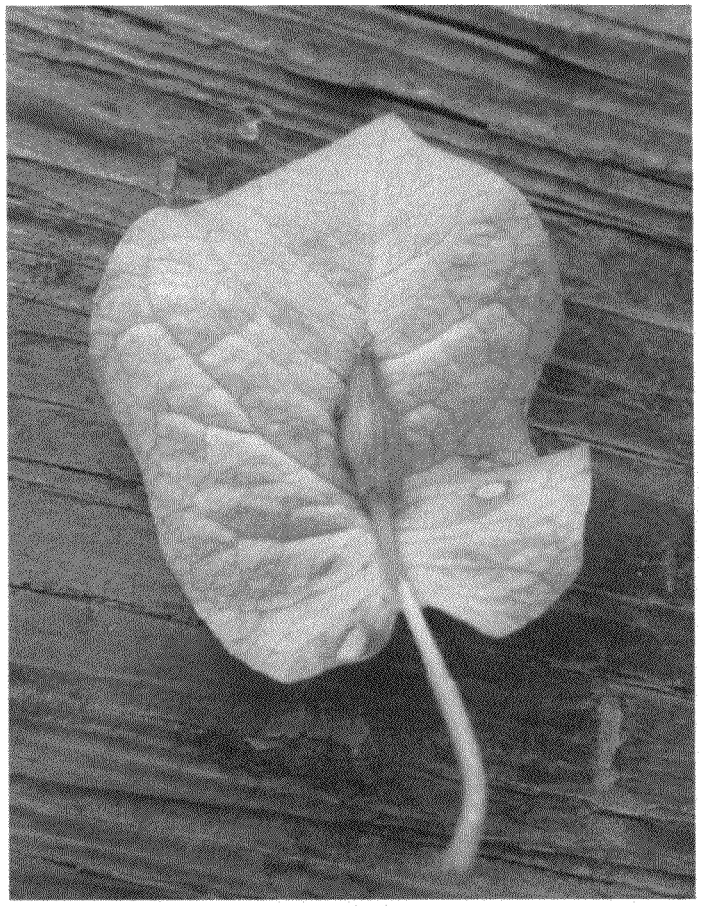
FIG. 2 shows a close-up a single bract and the reproductive organs taken in May 2014.
Figure 3:
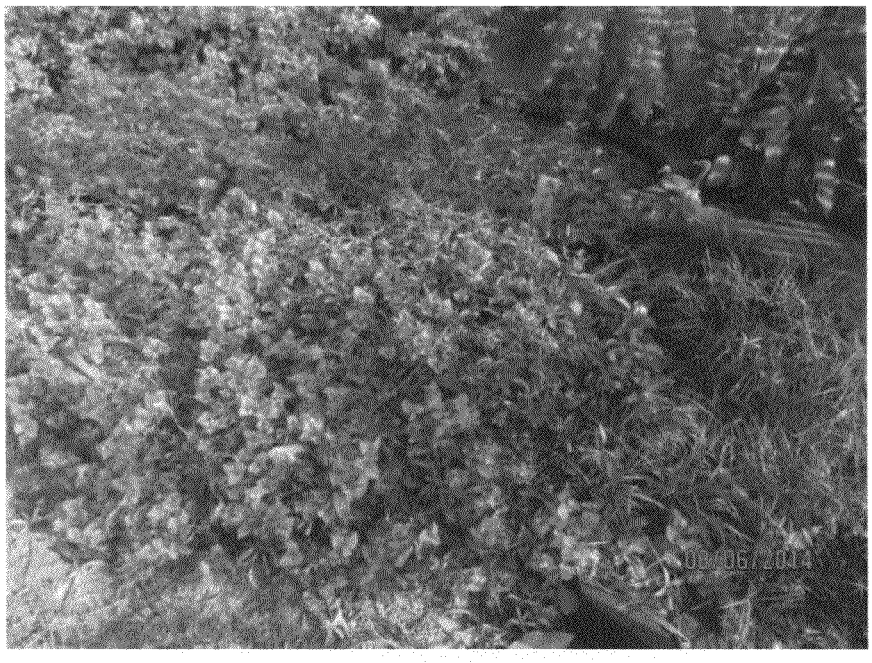
FIG. 3 shows the overall plant habit of 'IREBABS2' taken in June 2014.

The following detailed descriptions set forth the distinctive characteristics of 'IREBABS2'. The data which defines these characteristics were collected from asexual reproductions carried out in Brisbane, Australia. The plant history was taken in May 2013 on ten-year old plants grown outdoors in Brisbane, Australia. Color references were taken under natural light and are to The R.H.S. Colour Chart of The Royal Horticultural Society of London (R.H.S. 2005).

Classification:
- *Family*.—Nyctaginaceae.
- *Botanical name.—Bougainvillea×spectro-glabra.*
- *Common name.—Bougainvillea.*
- *Denomination*.—'IREBABS2'.

Plant:
- *Type*.—Shrub and perennial (in warmer climates).
- *Form*.—Rounded.
- *Habit*.—Low growing, prostrate, and spreading.
- *Appropriate containers*.—Commercial pots of all sizes.
- *Time to produce a finished flowering plant*.—12 weeks from a cutting.
- *Growth rate*.—Moderate.
- *Vigor*.—Good — strong.
- *Height* (*measured from the top of the soil*).—60.0 cm to 70.0 cm.
- *Width* (*horizontal plant diameter*).—Up to 100.0 cm.
- *Pinching required*.—Yes, at liner stage.
- *Propagation type*.—Cuttings.

Lateral branches:
- *Branching habit*.—Horizontal.
- *Diameter*.—0.3 cm to 0.5 cm.
- *Internode length*.—0.7 cm to 1.5 cm.

*Aspect*.—Horizontal.
*Strength*.—Strong.
*Color*.—RHS 191A.
*Pubescence*.—Absent.
*Thorns*.—General: Minimal and mainly on older wood and last season growth. Size: 0.4 cm to 0.6 cm in length. Quantity: 2 per inch. Color: RHS 191A (Greyed-Green).

Foliage:
*Arrangement*.—Alternate, single.
*Durability of foliage to stresses*.—Strong.
*Quantity of leaves per lateral branch*.—28 to 30.
*Shape*.—Ovate.
*Apex*.—Acuminate.
*Base*.—Shortly attenuate.
*Margin*.—Smooth, entire.
*Length*.—5.0 cm to 5.3 cm.
*Diameter*.—2.9 cm to 3.5 cm.
*Color, immature*.—Upper surface: RHS 137A. Lower surface: RHS 137C.
*Color, mature*.—Upper surface: RHS 139A. Lower surface: RHS 138A.
*Texture*.—Both upper and lower surfaces: Smooth.
*Venation type*.—Pinnate.
*Venation color*.—Upper surface: RHS 139A. Lower surface: RHS 138A.
*Petiole*.—Length: 1.1 cm to 1.3 cm. Diameter: 0.1 cm to 0.15 cm. Color: RHS 138A.

Spines: Present.

Inflorescence:
*General*.—Flowers all along the branch — branchlets with flowers at each node.
*Width*.—15.0 cm to 15.6 cm.
*Bud*.—Shape: Urn-shaped. Length: 0.6 cm to 1.2 cm. Diameter: 0.6 cm to 0.8 cm. Color: RHS 59A.
*Flower*.—Type and habit: Single flowers arranged in axillary panicles; flowers are upright and self-cleaning; ruffled at the base. Fragrance: Absent. Aspect: Upright. Flowering season: Profuse flowering; flowers in autumn, the spring and regions with mild winters. Diameter: 2.3 cm to 2.5 cm. Depth: 2.6 cm to 2.9. Quantity per lateral stem: About 87 to 90. Quantity of flowers per inflorescence: 8 to 10. Flower: General: Flower throat is tubular in shape, slender; *Bougainvillea* inflorescence consists of three fused and colored bracts with three flowers having fused petals. Length: 1.8 cm to 2.0 cm. Color, immature, outer surface, closed: RHS 184B with RHS 184C at the top. Color, mature, fully opened: Outer surface: RHS 162C (Greyed-Yellow) with rays of RHS 184D (Greyed-Purple). Inner surface: RHS 160B to RHS 160D (Greyed-Yellow) with RHS 145B (Green) and RHS 184D (Greyed-Purple) striations between the fused petals. Bracts: Quantity per flower: 1 flower per bract in group of 3. Length: 3.0 cm to 3.2 cm. Width: 2.6 cm to 2.8 cm. Shape: Broadly ovate. Apex: Shortly acuminate. Base: Cordate. Margin: Entire. Texture (upper and lower surfaces): Velvety. Color, when opening: Upper surface: RHS 58A. Lower surface: RHS 61A. Color, when open: Upper surface: RHS 180A. Lower surface: RHS 61C. Fading to: RHS 180C. Peduncle: Length: 1.6 cm to 2.0 cm. Diameter: 0.1 cm to 0.15 cm. Angle: 25°. Strength: Strong. Color: RHS 138B. Pedicel: Length: 3.0 cm to 3.5 cm. Diameter: 0.1 cm to 0.17 cm. Angle: 30°. Strength: Moderate. Color: RHS 138B.

Reproductive organs:
*Anther color*.—RHS 155A (White).
*Pollen color*.—Too small to determine.
*Number of pistils per flower*.—1.
*Pistil length*.—0.7 cm.
*Stigma shape*.—Tapering wedge shape.
*Stigma color*.—RHS 151A (Yellow-Green).
*Style length*.—3.0 cm.
*Style color*.—RHS 151A (Yellow-Green).
*Ovary color*.—RHS 151A (Yellow-Green).

Fruit and seed set: Rarely observed, but 1 seed per flower if fertile; 0.3 cm length, 0.13 cm diameter, RHS 177D.

Disease and insect resistance: No specific disease or insect resistance observed.

COMPARISON WITH PARENTAL AND COMMERCIAL VARIETY

'IREBABS2' differs from the female *Bougainvillea* parent 'Kayata' (unpatented) in that 'Kayata' has a taller growing plant habit than 'IREBABS2'.

'IREBABS2' differs from the commercial comparison 'Kasumi' (U.S. Plant Pat. No. 22,113) in that 'IREBABS2' has rose-colored bracts, while 'Kasumi' has salmon-pink bracts.

We claim:

1. A new and distinct variety of *Bougainvillea* plant as illustrated and described herein.

* * * * *